(12) United States Patent
Shvetsov et al.

(10) Patent No.: US 12,274,488 B2
(45) Date of Patent: Apr. 15, 2025

(54) ELECTROSURGICAL DEVICE WITH VACUUM PORT

(71) Applicant: Buffalo Filter LLC, Lancaster, NY (US)

(72) Inventors: Kyrylo Shvetsov, Depew, NY (US); Anthony Lizauckas, III, Williamsville, NY (US); Gregory Pepe, Lancaster, NY (US); Daniel R Palmerton, Elma, NY (US); Joseph Lynch, Williamsville, NY (US); Christopher A Palmerton, Clarence, NY (US); Samantha Bonano, Williamsville, NY (US)

(73) Assignee: Buffalo Filter LLC, Lancaster, NY (US)

( * ) Notice: Subject to any disclaimer, the term of this patent is extended or adjusted under 35 U.S.C. 154(b) by 132 days.

(21) Appl. No.: 17/738,595

(22) Filed: May 6, 2022

(65) Prior Publication Data
US 2022/0257306 A1   Aug. 18, 2022

Related U.S. Application Data

(63) Continuation of application No. 13/840,693, filed on Mar. 15, 2013, now Pat. No. 11,357,564.
(Continued)

(51) Int. Cl.
*A61B 18/14* (2006.01)
*A61B 90/30* (2016.01)
(Continued)

(52) U.S. Cl.
CPC .......... *A61B 18/1402* (2013.01); *A61B 90/30* (2016.02); *A61B 90/98* (2016.02);
(Continued)

(58) Field of Classification Search
None
See application file for complete search history.

(56) References Cited

U.S. PATENT DOCUMENTS

| 3,825,004 A | 7/1974 | Durden |
| 5,085,657 A | 2/1992 | Ben-Simhon |

(Continued)

FOREIGN PATENT DOCUMENTS

GB    2406793 A    4/2005

*Primary Examiner* — Kennedy Schaetzle
(74) *Attorney, Agent, or Firm* — Timothy W. Menasco, Esq.; Harter Secrest & Emery LLP

(57) ABSTRACT

An electrosurgical device comprising: an electrode having a first portion whose exterior is electrically uninsulated, a second portion whose exterior is electrically insulated, and a third portion; an elongated hollow body having an internal cavity, a front end, a rear end, an external surface, and an electrical wire arranged within the body. The hollow body is configured to reversibly receive the third portion of the electrode at the front end of the body such that electrical contact is made between the electrode and the electrical wire and the second portion of the electrode is not surrounded by the hollow body. A first button is provided for controlling a current flow at a first level to the electrode and is arranged on the external surface. A vacuum tube is slidably engaged by the body and has an inlet generally facing the front end and adjacent the electrode. A vacuum outlet port is arranged near the rear end of the body, and the outlet port, internal cavity, and vacuum inlet are in fluid communication with each other.

20 Claims, 15 Drawing Sheets

Related U.S. Application Data

(60) Provisional application No. 61/645,051, filed on May 9, 2012.

(51) Int. Cl.
 *A61B 90/98* (2016.01)
 *A61B 18/00* (2006.01)

(52) U.S. Cl.
 CPC ............ *A61B 2018/00922* (2013.01); *A61B 2218/008* (2013.01)

(56) References Cited

U.S. PATENT DOCUMENTS

| | | |
|---|---|---|
| 5,192,267 A | 3/1993 | Shapira et al. |
| 5,234,428 A | 8/1993 | Kaufman |
| 5,269,781 A | 12/1993 | Hewell |
| 5,318,565 A * | 6/1994 | Kuriloff ............ A61B 18/1402 606/49 |
| 5,413,575 A | 5/1995 | Haenggi |
| 5,626,568 A | 5/1997 | Yeh et al. |
| 5,709,675 A | 1/1998 | Williams |
| 5,730,742 A | 3/1998 | Wojciechowicz |
| 5,836,944 A | 11/1998 | Cosmescu |
| 6,146,353 A | 11/2000 | Platt |
| 6,635,034 B1 | 10/2003 | Cosmescu |
| 6,733,495 B1 | 5/2004 | Bek et al. |
| 9,289,261 B2 * | 3/2016 | Shvetsov ............ A61B 18/1402 |
| 10,405,917 B2 | 9/2019 | Shvetsov et al. |
| 11,357,564 B2 | 6/2022 | Shvetsov et al. |
| 11,589,917 B2 | 2/2023 | Shvetsov et al. |
| 2001/0018586 A1 | 8/2001 | Cosmescu |
| 2002/0019596 A1 | 2/2002 | Eggers et al. |
| 2004/0162553 A1 | 8/2004 | Peng et al. |
| 2005/0060974 A1 | 3/2005 | Palmerton et al. |
| 2006/0264928 A1 | 11/2006 | Kornerup et al. |
| 2009/0018539 A1 | 1/2009 | Comescu |
| 2009/0054890 A1 | 2/2009 | De Carlo |
| 2009/0062791 A1 | 3/2009 | Lee et al. |
| 2010/0130972 A1 | 5/2010 | Yambor et al. |
| 2010/0145333 A1 | 6/2010 | Dethier et al. |
| 2011/0190768 A1 * | 8/2011 | Shvetsov ............ A61B 90/30 606/48 |
| 2012/0067212 A1 | 3/2012 | Warren et al. |
| 2012/0203208 A1 * | 8/2012 | Minskoff ............ A61M 1/7411 606/45 |
| 2012/0286179 A1 | 11/2012 | Palmerton et al. |
| 2014/0303449 A1 | 10/2014 | Balog |

* cited by examiner

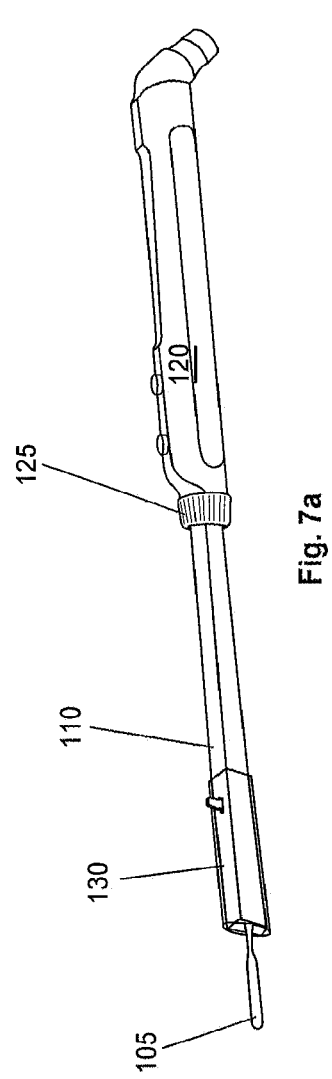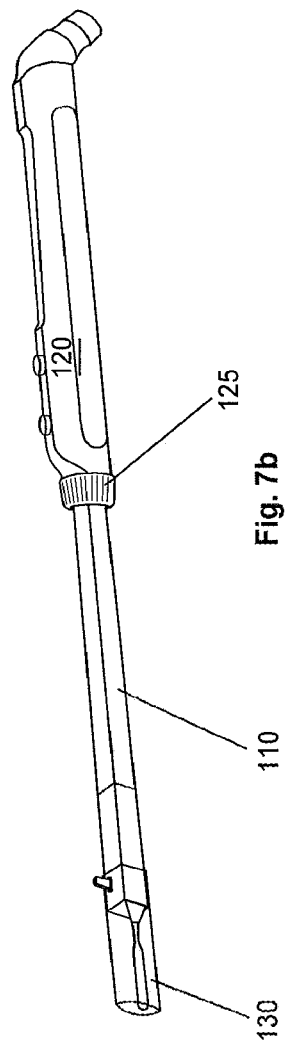

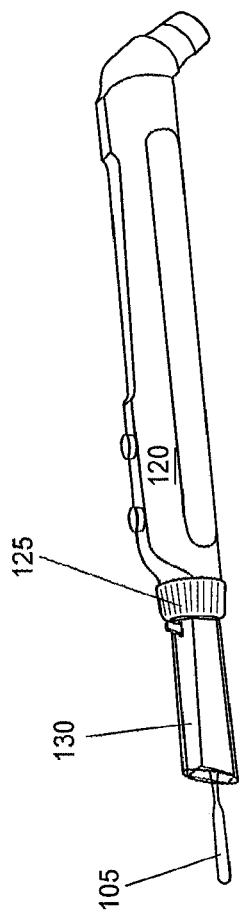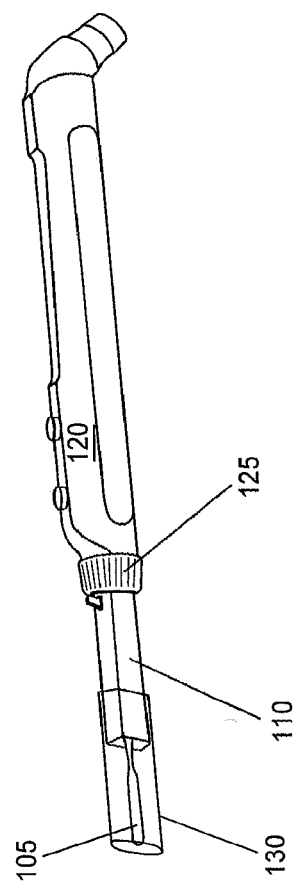
Fig. 8a
Fig. 8b

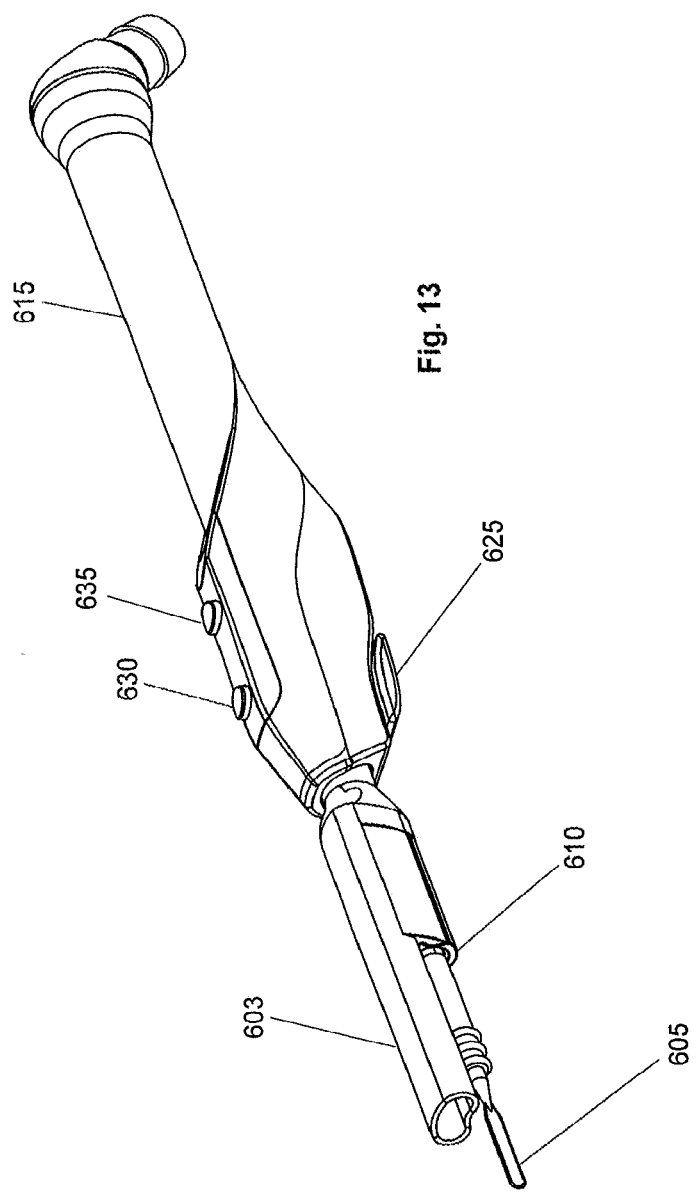

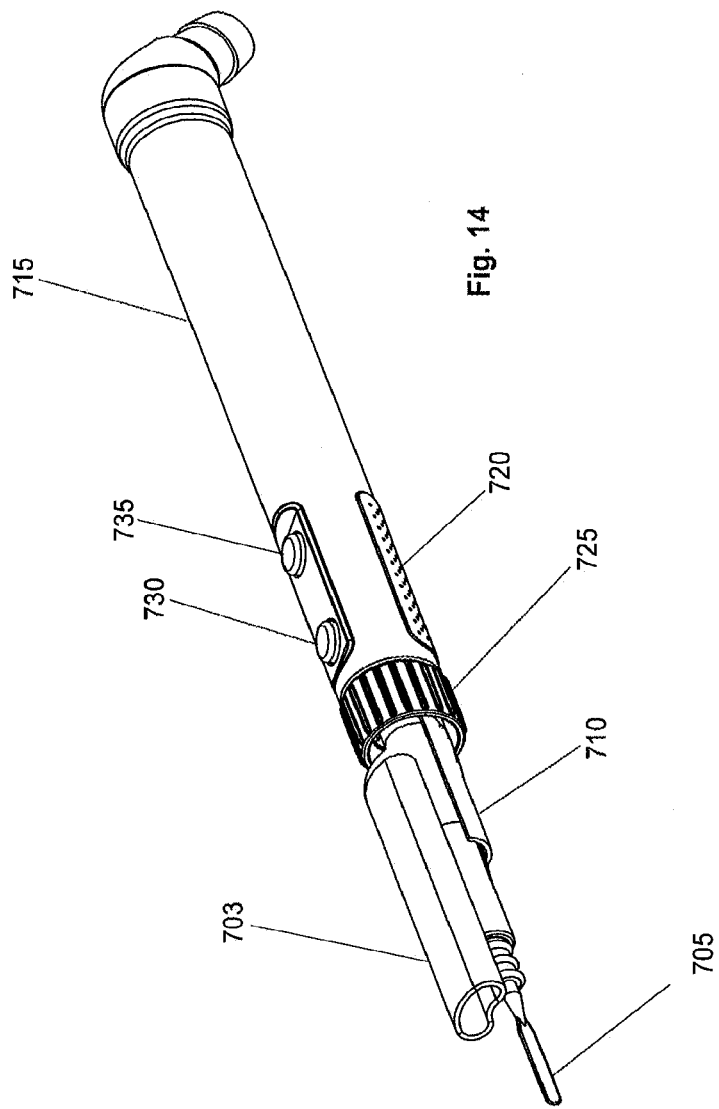

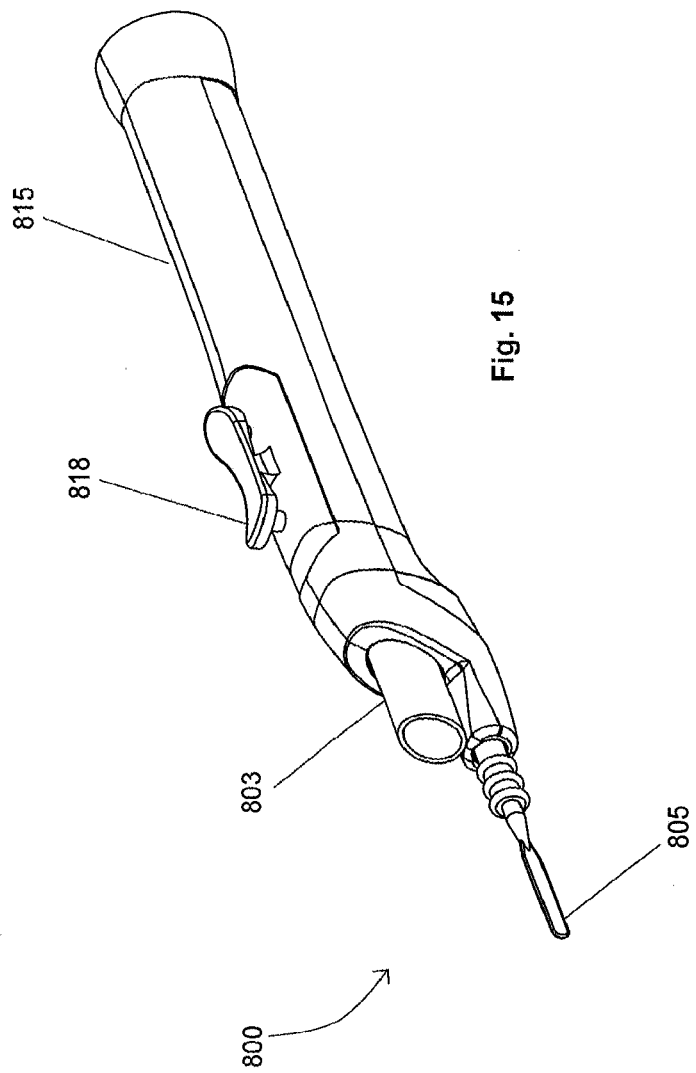

ELECTROSURGICAL DEVICE WITH VACUUM PORT

CROSS-REFERENCE TO RELATED APPLICATIONS

This application claims priority benefit of U.S. Provisional Application No. 61/645,051, filed on May 9, 2012, which is incorporated herein by reference in its entirety.

TECHNICAL FIELD

The present invention relates generally to smoke evacuation and, more specifically, to an electrosurgical device with smoke evacuation during medical procedures.

BACKGROUND

Surgical smoke and aerosol, or plume, is created in connection with surgery. For example, when laser or electrosurgical energy is delivered to a cell, heat is created. This heat vaporizes the intracellular fluid, which increases the pressure inside the cell and eventually causes the cell membrane to burst. In this example, a plume of smoke containing water vapor is released into the atmosphere of the operating room or doctor's office. At the same time, the heat created may char the protein and other organic matter within the cell, and may cause thermal necrosis in adjacent cells. The charring of cells may also release other harmful contaminants, such as carbonized cell fragments and gaseous hydrocarbons.

BRIEF SUMMARY OF THE INVENTION

With reference to the corresponding parts portions or surfaces of the disclosed embodiment, merely for the purposes of illustration and not by way of limitation, an electrosurgical device (50) is provided having: an elongated hollow body (22) having an internal cavity (66), a front end, a rear end, an external surface, and an electrical conductor (27, 85) arranged within the body, the hollow body configured to reversibly receive the a portion of an electrode (12) at the front end of the body such that an electrical contact may be made between the electrode and the electrical conductor, in which the body is configured and arranged such that an insulated portion of a received electrode is not surrounded by the hollow body, a first button (18) arranged on an external surface of the body for controlling a current flow through the electrical conductor at a first level, a vacuum tube (16) slidably engaged by the body and having an inlet (15) generally facing the front end of the body, the vacuum tube arranged adjacent to the electrode, a vacuum outlet port (24) arranged near the rear end, and in which the outlet port, internal cavity, and vacuum inlet are in fluid communication with each other.

The body may be ergonometrically shaped to be received by a user's hand.

The body may be generally pencil shaped and includes friction texture on an outer surface.

The electrode may be one of a monopolar, bipolar, or sesquipolar electrode.

The electrosurgical device may further have a second button for controlling a current flow at a second level through the electrode.

The electrosurgical device may further have a third button to control a vacuum source.

The electrosurgical device may further have a light source arranged to illuminate an area near the electrode.

The electrosurgical device may further have a battery for providing power to the light source.

The electrosurgical device may further have a button for controlling the light source.

The electrosurgical device may further have a swivel joint between the body and the outlet port.

The electrosurgical device may further have an electrical line passing through the swivel joint.

The electrosurgical device may further have a filter arranged within the internal cavity.

The filter may have an RFID tag containing filter information.

The vacuum inlet may have a generally rectangular cross section.

The vacuum inlet comprises a circular cross section.

The vacuum inlet may have an outward flared intake opening.

The button may have an indicator light which turns on when the button may be depressed.

The indicator light may be an LED.

The electrosurgical device may further have a second button, the second button having an indicator light, each the indicator light having a different color The light source may be powered from a generator attached to the electrosurgical device.

The light source may be powered by a current flow in the electrical conductor.

The light source may be powered by an internal capacitor, the internal capacitor charged by a current flow in the electrical conductor during an electrosurgical device activation.

The vacuum tube inlet may have a shape that has a larger cross section than the cross section of the rest of the vacuum tube.

The vacuum tube inlet has an inverted "U" shape which extends around the electrode.

The first button may be a rocker switch.

The rocker switch comprises a first state for a first current level and a second state for a second current level.

The body may have a first rigid material and a second material, and the second material may be arranged on a portion of an outer surface of the body.

The second material may be a material softer than the first material.

The second material may be a material with a higher surface friction coefficient than the first material.

In another aspect, an electrosurgical device is provided having: an electrode, an elongated hollow body having an internal cavity, a front end, a rear end, an external surface, and a retractable electrode mount slidably arranged within the body, the electrode mount configured and arranged to reversibly receive the electrode, a first button for controlling a current flow at a first level to the electrode and arranged on the external surface, a vacuum tube slidably engaged by the body and having an inlet generally facing the front end, the vacuum tube surrounding the electrode mount, a vacuum outlet port arranged near the rear end of the body, and in which the outlet port, internal cavity, and vacuum inlet are in fluid communication with each other.

The hollow body may be shaped to have an ergonometric orientation complementary to a user's hand.

The vacuum tube comprises a clear material.

The clear material comprises plastic or glass.

The retractable electrode mount may be compressively engaged by the body.

The body comprises a compression screw for increasing a compression of the electrode mount by the body for locking an electrode mount position.

The body comprises a slide for increasing a compression of the electrode mount by the body for locking an electrode mount position.

The body comprises a lever increasing a compression of the electrode mount by the body for locking an electrode mount position.

The body comprises a locking means for locking an electrode mount position.

The vacuum tube compressively engages the electrode mount.

The electrode mount, vacuum tube, and the body are in a telescopic arrangement.

The device may be configured and arranged such that an electrically insulated portion of the electrode may be not surrounded by the body when the electrode may be received by the body.

The body may be generally pencil shaped and comprises friction texture on a surface.

The electrode comprises a monopolar, bipolar, or sesquipolar electrode.

The electrosurgical device may further have a second button for controlling a current flow at a second level to the electrode.

The electrosurgical device may further have a third button for controlling a vacuum source.

The inlet may have a generally rectangular cross section.

The inlet may have a circular cross section.

The electrosurgical device may further have a light source arranged to illuminate an area near the electrode; a battery for providing power to the light source; a button for controlling the light source.

The electrosurgical device may further have a swivel joint between the body and the outlet port.

The electrosurgical device may further have an electrical line arranged to pass through the swivel joint.

The electrosurgical device may further have a filter arranged within the internal cavity.

The filter may have an RFID tag containing filter information.

In another aspect, an electrosurgical device is provided having: an electrode, an elongated hollow body having an internal cavity, a front end, a rear end, an external surface, and an electrical wire arranged within the body, the hollow body configured to reversibly receive the electrode, the hollow body shaped to have an ergonometric orientation complementary to a user's hand, a first button for controlling a current flow at a first level to the electrode arranged on the external surface, a vacuum tube engaged by the body and having an inlet generally facing the front end, the vacuum tube arranged adjacent the electrode and the inlet having a substantially vertical cross section when the device may be held in the ergonometric orientation, a vacuum outlet port arranged near the rear end, in which the outlet port, internal cavity, and vacuum inlet are in fluid communication with each other, means for preventing the vacuum tube from obstructing a user's view of the electrode, and means removing the electrode without electrically contacting the electrode.

The means for preventing the vacuum tube from obstructing a user's view may include a slidable engagement between the vacuum tube and the body.

The means for preventing the vacuum tube from obstructing a user's view may include a vacuum tube made of clear material.

The means for preventing the vacuum tube from obstructing a user's view may have an inlet shaped to have a cross section parallel to a user's line of sight towards the electrode when using the device.

The means for removing the electrode without electrically contacting may include configuring and arranging the body to hold an electrode such that a portion of the electrode with an insulation coating remains accessible to a user's hand.

BRIEF DESCRIPTION OF THE DRAWINGS

FIGS. 7*a* and 7*b* are side views of the third embodiment with a shroud in retracted and extended configurations.

FIGS. 8*a* and 8*b* are side views of the third embodiment in retracted and extended configurations.

FIG. 13 is a perspective view of a seventh embodiment of the electrosurgical device, and FIG. 14 is a perspective view of an eighth embodiment of the electrosurgical device.

FIG. 15 is a perspective view of a ninth embodiment of the electrosurgical device.

DETAILED DESCRIPTION OF THE PREFERRED EMBODIMENTS

Figure 1:
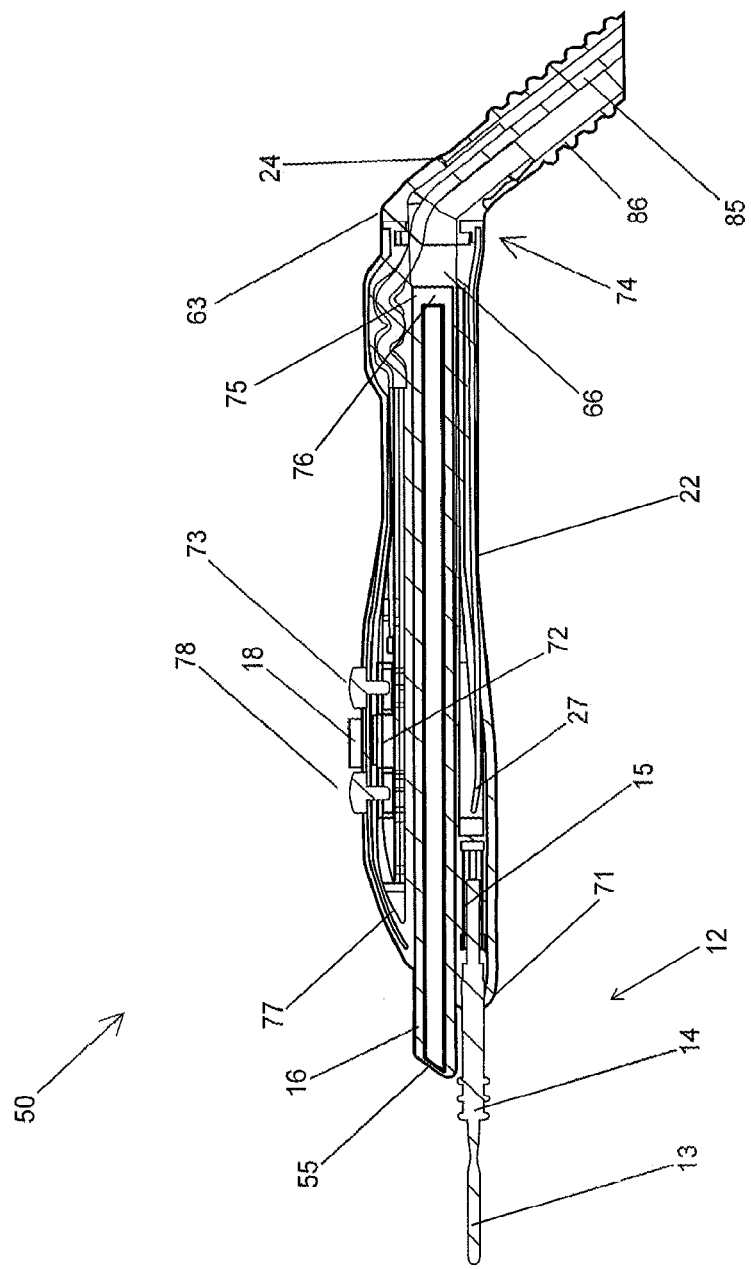
FIG. 1 is a section view of a first embodiment electrosurgical device.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

Referring now to the drawings, the present invention broadly provides an electrosurgical device, generally indicated at 50, which is particularly adapted for (but is not limited to) suctioning smoke during electrosurgery.

In FIG. 1, the electrosurgical device is shown as broadly including hollow body 22 with a front end holding electrode 12, a rear end holding vacuum port 24, electrical line 85, cut/coagulate rocker switch 18, and vacuum tube 16. Vacuum tube 16 is slidably engaged by hollow body 22 and is shown in the retracted configuration in FIG. 1.

Electrode 12 has uninsulated portion 13, connected to insulated portion 14. As shown in FIG. 1, insulated portion 14 contains circular ridges. Connected to insulated portion 14 is uninsulated portion 13 which is reversibly and compressively engaged by hollow body 22. When engaged by hollow body 22, electrode 12 makes electrical contact with internal wire 27 which is connected to electrical line 85 through rocker switch 18 within elongated body 22. Also, when electrode 12 is engaged to body 22, portion 14 of electrode 12 extends out of body 22 and can be easily gripped by a user's fingers.

Internal wire 27 within elongated body 22 extends from rocker switch 18 to the rear of body 22. At the rear of body 22 electrical line 85 exits body 22 adjacent to vacuum exit port 24.

Vacuum tube 16 has an inlet 55 facing generally towards the front end of body 22. In this embodiment the outer surface of inlet 15 is angled downward and leftwards towards electrode 12's front end as shown in FIG. 1. However, in other embodiments, the cross section of inlet 15 is angled upwards and leftwards and is generally rectangular shaped. Vacuum tube 16 is compressively engaged by hollow cavity 66 of body 22. Vacuum tube 16 is capable of telescopically extending from and retracting into cavity 66. However, even when fully retracted, a portion of vacuum tube 16 will be protruding from body 22 and can be laterally gripped by a user.

Vacuum tube 16 is in fluid communication with hollow cavity 66 and vacuum exit port 24. Elongated body 22 contains bend 63 in its body near vacuum port 24 as shown in FIG. 1. The interface between bend 63 and vacuum exit port 24 forms a swivel joint.

Figure 2:
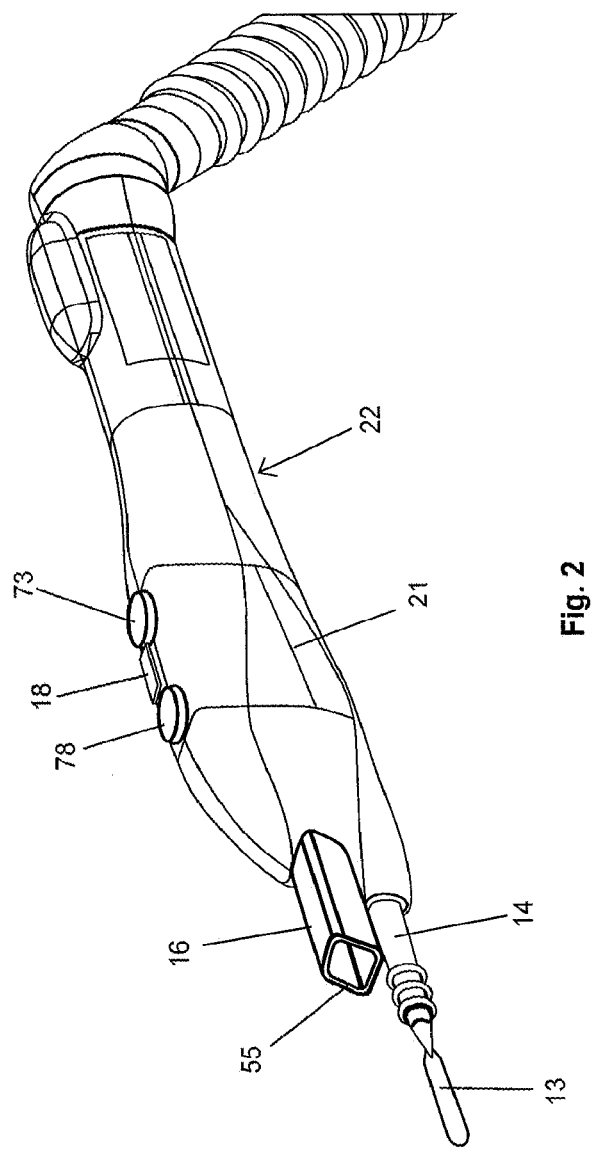
FIG. 2 is perspective view of the first embodiment.

On the exterior lateral surfaces of body 22 are friction textures 21, as shown in FIG. 2. On the top surface of body 22 is rocker switch 18, which is configured to activate a coagulation mode when rocked forwards and a cutting mode when rocked backwards. In other embodiments, rocker switch 18 can be replaced by a cut button and/or a coagulate button.

Vacuum tube 16 is made of clear plastic. The colors of rocker switch 18, body 22, and electrode insulated portion 14 are all distinct. Wire 27 and 85 are flexible.

Also shown in FIG. 1, electrosurgical device 50 contains illumination light 71, light toggle button 78, and light battery 72 for providing greater illumination of the surgical region. Swivel joint 74 is arranged on the front facing side of bend 63. Embodiment 50 further contains filter 75 within hollow cavity 66. Filter 75 help remove particulate matter, moisture, and odor from the plume suctioned. The filter contains RFID tag 76 which contains filter information as well as provides a tracking ID for the electrosurgical device. Also, vacuum control button 73 allows the vacuum source to be switched on and off manually directly on the electrosurgical device. RF sensor 77, which is electrically isolated from the electrosurgical power source, is connected to a remote vacuum source controller which is configured to automatically turn the vacuum source on when sensor 77 detects RF energy from either the cut of coagulate modes.

FIGS. 1 and 2 show first embodiment with vacuum tube 16 in the retracted configuration. In the extended configuration, inlet 55 is positioned closer to electrode portion 13.

A user first prepares first embodiment 55 by inserting electrode 12 into the front end of elongated body 22. By holding electrode 12 by its insulated portion 14, the circular ridges along insulated portion 14 provide increased friction and grip for inserting electrode 12 into body 22. Electrode 12 is firmly pressed into body 22 such electrode 12 makes electrical contact with internal wire 27 within body 22. Since insulated portion 14 extends outside body 22 when electrode 12 is fully inserted, the user is able to insert the electrode without ever touching uninsulated portion 13 of electrode 12.

The user next adjusts vacuum tube 16 to the proper extension distance. The lateral edges of vacuum tube 16 are not hindered by body 22 and the user can easily grip vacuum tube 16 by the lateral edges and telescopically adjust the vacuum tube to an appropriate extension amount.

An external vacuum tube is connected to outlet port 24, insuring that outlet port 24 is securely inserted such that an air-tight seal is formed. The opposing end of the external vacuum tube is connected to a vacuum source, and electrical line 85 is connected to an electrosurgical RF power source.

In preparation for electrosurgery, the user will grip body 22 similar to holding a pencil, and the user's thumb and non-index fingers will be placed on opposite sides of body 22 along finger friction texture 21. As shown in FIG. 2, the shape of the device is ergonometrically suited to a user's hand. When the user is ready to initiate electrosurgery, the vacuum source will be toggled on by pressing vacuum control button 73. If illumination is desired, toggle button 78 is pressed to turn on illumination light 71. Rocker switch 18 will next be pressed either forwards or backwards with a user's index finger to cause wither a cutting or a coagulation mode to be initiated. Pressing button 18 will cause current to pass from electrical line 85 to internal wire 27 and out electrode 12 to a patient's body. The electrical current through the tissue causes intense heat and smoke, typically causing cutting or coagulation of tissue.

Smoke produced during electrosurgery is suctioned by vacuum tube 16. During surgery, the user may easily adjust vacuum tube 16's position, either extending it closer to electrode portion 13 in order better capture smoke, or retracting it closer towards body 22 in order to provide the user with a less obstructed view of the surgical area. The average current level for coagulate will be less than for cutting.

Since vacuum tube 16 is arranged above electrode portion 13, it is in a good position to capture smoke which typically travels upwards from the treatment region. In this position above the electrode, vacuum tube 16 is more likely to capture smoke than if it were arranged under electrode 13. Additionally, since vacuum tube is not on the bottom side of body 22, there is decreased risk of vacuum inlet 15 coming into contact with the patient's body which could cause trauma.

During the surgery, whenever the user's hand rotates along the elongated body's longitudinal axis, the swivel between bend 23 and outlet port 24 allows torsional strain to be released. If during the surgery a different electrode style is needed, the user may easily pull electrode 12 off of body 22. Since insulated portion 14 of electrode 12 is easily accessible to the user's fingers, the user may easily remove electrode 12 without touching electrically uninsulated areas of the electrode. This is an added safety feature to help prevent the user from being burned from unanticipated activation of the electrosurgical device. The circular friction ridges along insulated portion 14 and friction texture 21 along elongated body 22 also help to provide increased stability during the process of removing and inserting electrodes.

Since electric line 85 passes through vacuum port 24, it will not wrap around the external vacuum tube when the electrosurgical device is twisted relative to the external vacuum tube. This reduces the chance of discomfort for the user by preventing rotational strains on the user's movement.

As shown, vacuum inlet 55 is angled such that when the device is held correctly during surgery, the cross section of the nozzle will be substantially parallel to the user's line of sight as the user looks at the treatment area. In this arrangement, vacuum inlet 55 can be placed as close as possible to the treatment area without obstructing the user's view. For example, in this configuration, both the top of the nozzle and the bottom of the nozzle are right up flush with the user's line of sight, as close as possible to the smoke creation region before starting to obstruct the user's view.

Additionally, as shown in FIG. 1, vacuum tube 16 has a rectangular shaped cross section. While the rectangular cross section allows for the complete electrosurgical device to have a shorter vertical profile, a crescent shaped cross section in alternative embodiments allows the vacuum tube to more closely enclose the electrode to increase the chances of more completely sucking up the created smoke. The shorter vertical profile makes the electrosurgical device easier to handle.

Figure 3:
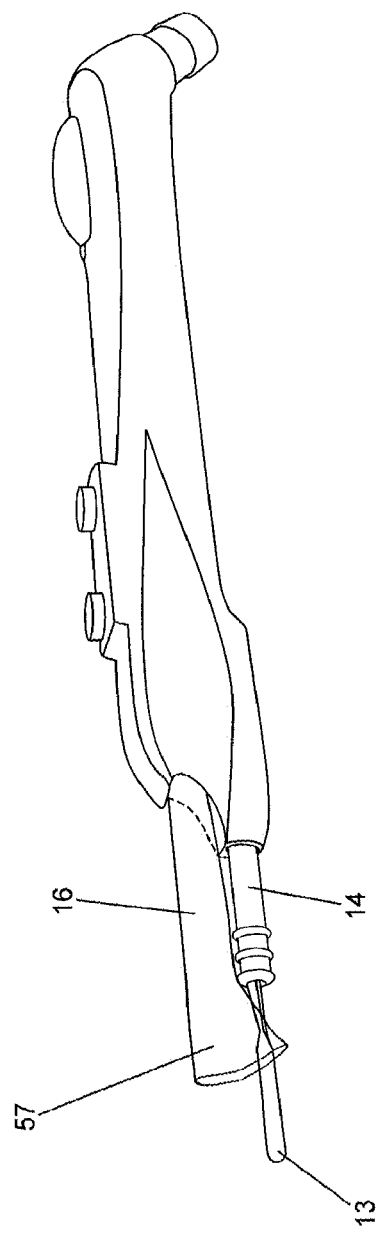
FIG. 3 is a side view of a second embodiment with a flared vacuum tube inlet.
Figure 4:
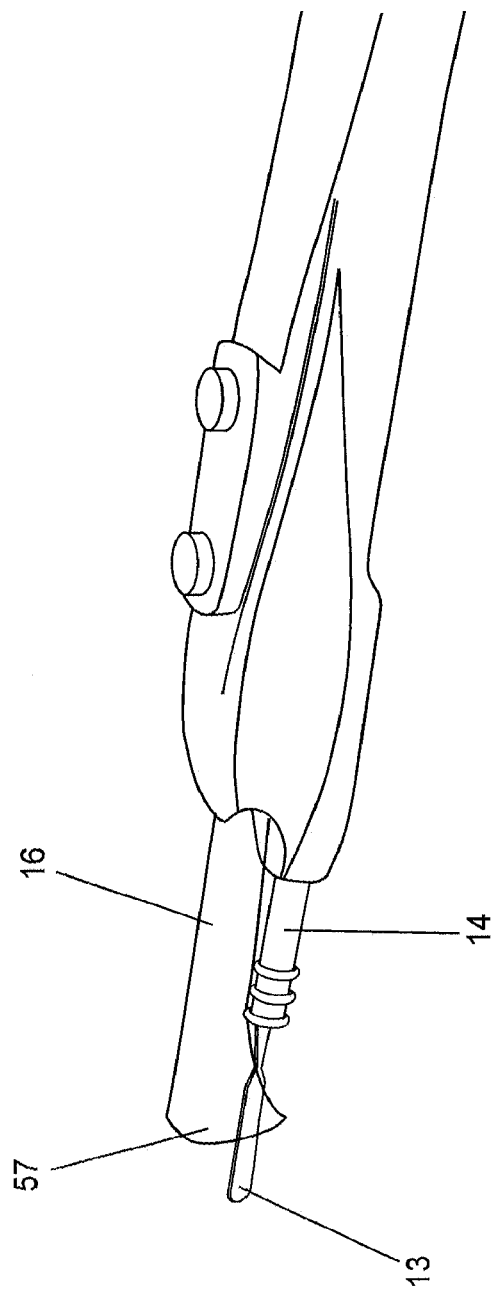
FIG. 4 is a perspective view of the second embodiment with a flared vacuum tube inlet.
Figure 5:
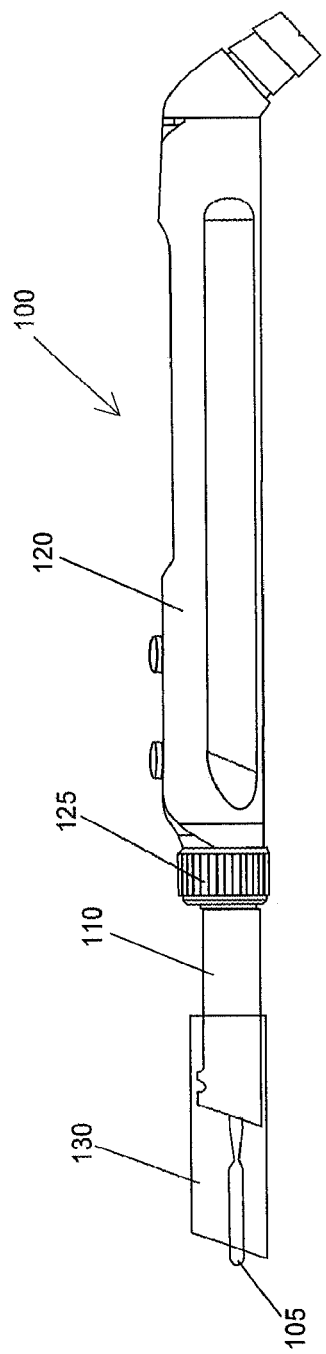
FIG. 5 is a side view of a third embodiment having a retractable electrode mount and a vacuum tube which surrounds the electrode mount.
Figure 6:
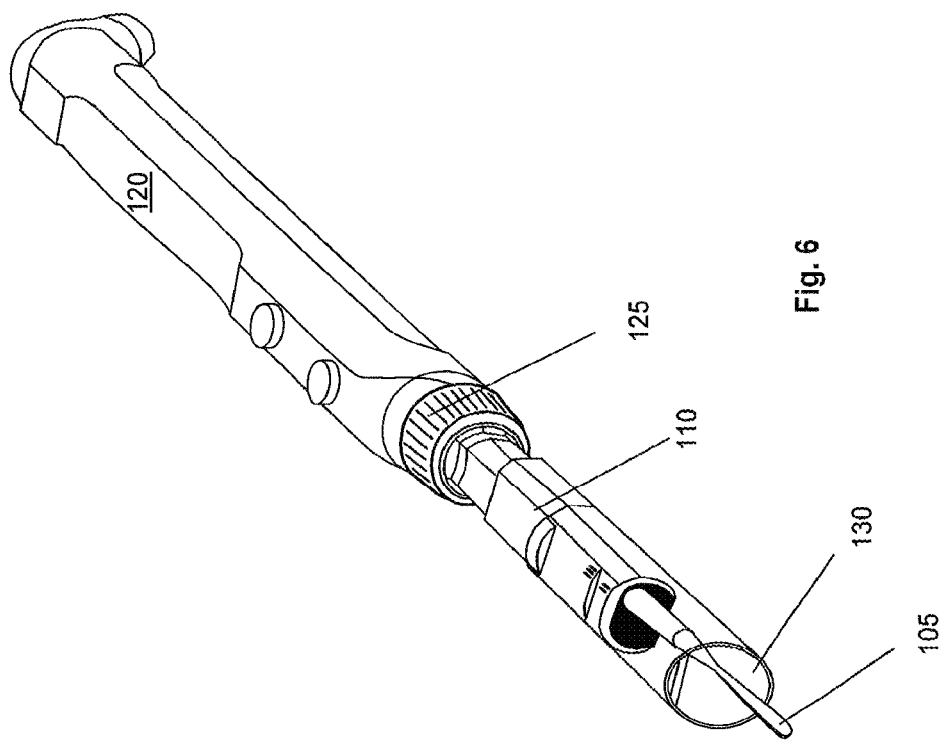
FIG. 6 is a perspective view of the third embodiment.
Figure 9:
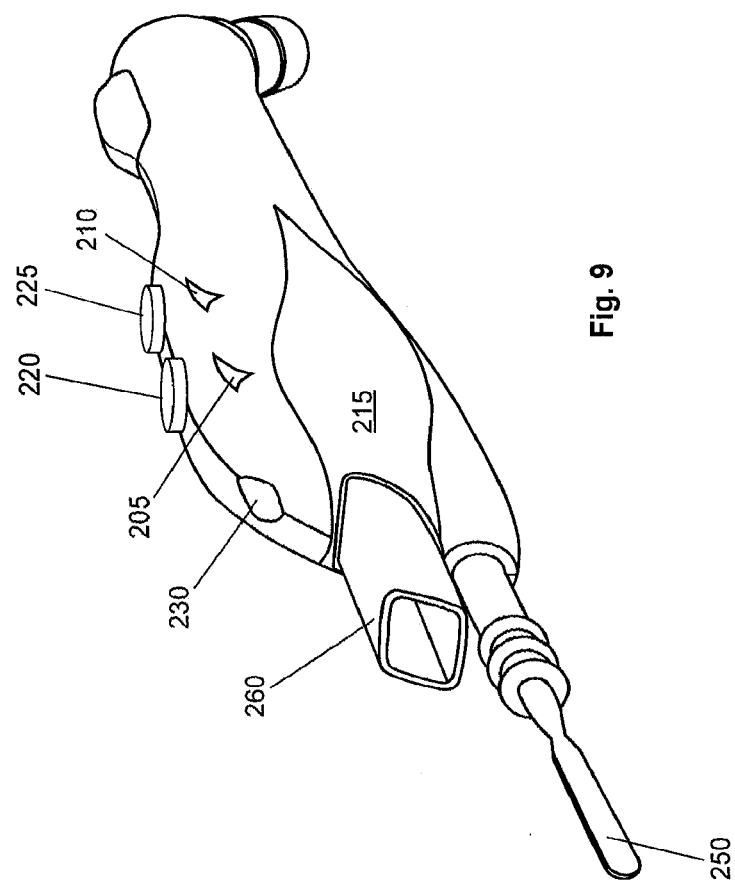
FIG. 9 is a perspective view of a fourth embodiment with indicated indicator lights for the buttons.
Figure 10:
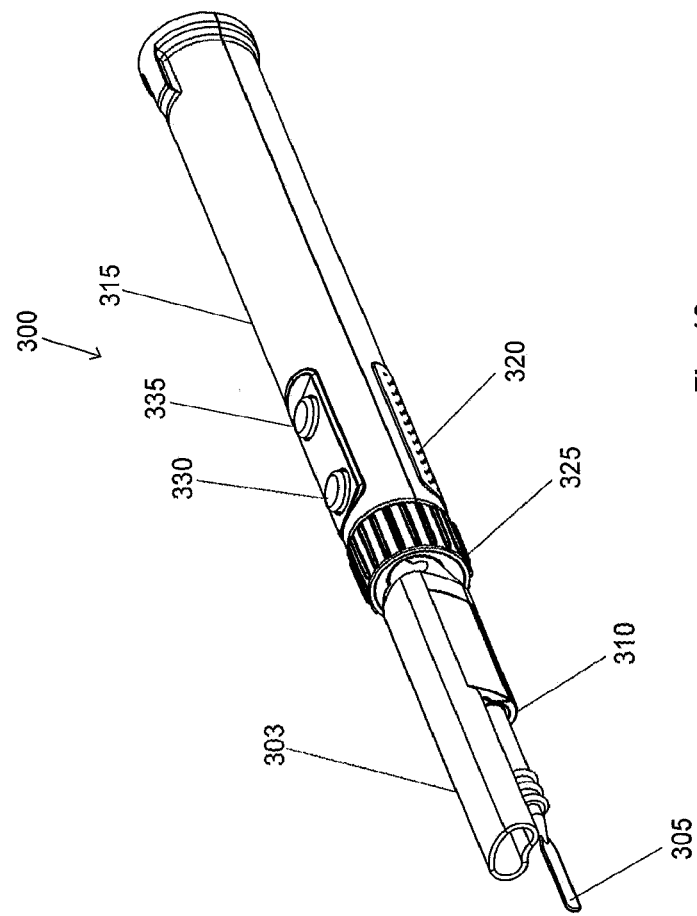
FIG. 10 is a perspective view of a fifth embodiment of the electrosurgical device.
Figure 11:
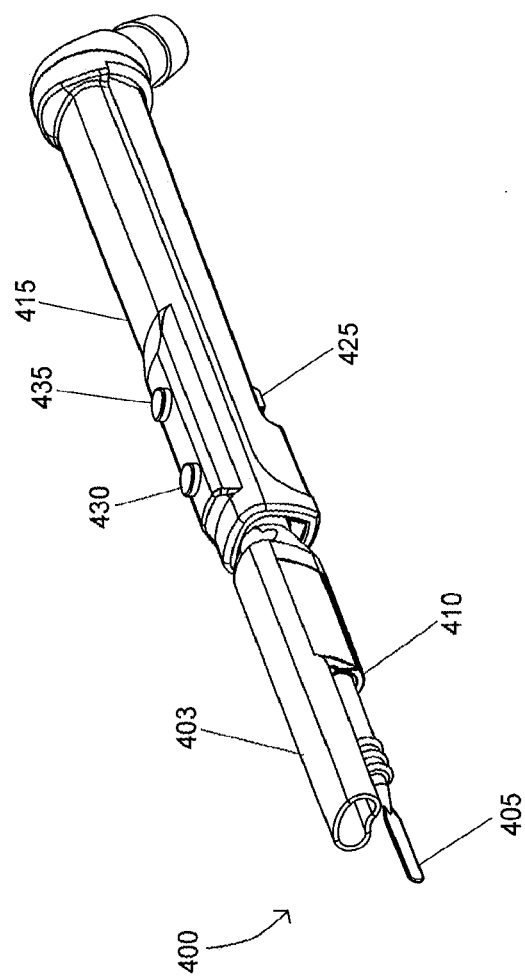
FIG. 11 is a perspective view of a sixth embodiment of the electrosurgical device and FIG. 12 is a perspective view of a seventh embodiment of the electrosurgical device.
Figure 12:
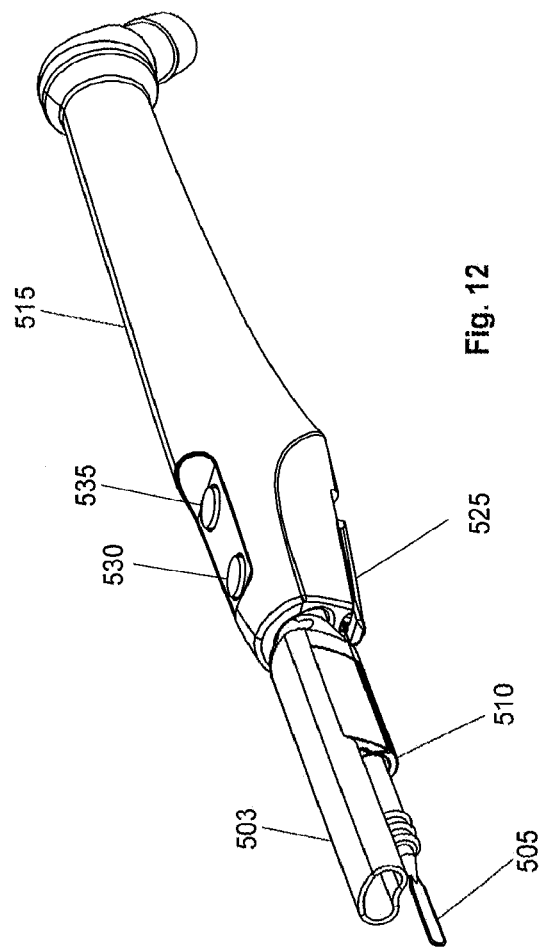

In FIGS. 3 and 4, the vacuum tube 16 is provided with a flared section 57 at the vacuum tube inlet 55. Turning to FIGS. 5-8b, in an alternate embodiment electro-surgical device 100 has an electrode 105 that is placed inside the vacuum tube 110. The vacuum tube 110 slides in and out of the body 120 and is fixed in position by means of an IC medical twist front 125. The vacuum tube 110 has a shroud 130 disposed at the end. The shroud 130 can slide forward and backward from the blade to increase or decrease blade coverage. FIGS. 7a-7b show the vacuum tube 110 in an extended position with respect to the body 120. In FIG. 7a, the shroud 130 is retracted and in FIG. 7b, the shroud 130 is extended to cover the electrode 105. In FIGS. 8a and 8b, the vacuum tube 110 is retracted. In FIG. 9 in a fourth embodiment, electrosurgical device 200 includes indicator lights 205, 210 mounted on the body 215. A different light is activated depending on which button 220, 225 is pressed. A forward looking white light-emitting diode (LED) 230 can be activated when either of the buttons 220, 225 is pressed. The electrosurgical device 200 also includes an electrode 250 and a vacuum tube 260. In FIG. 10 electrosurgical device 300 includes a vacuum tube 303 disposed above an electrode 305. The electrode 305 is supported by an electrode holder 310. The body 315 of the device 300 has a grip 320 disposed thereon. The vacuum tube 303 slides in and out of the body 315 and can be locked into position by a twist lock 325. In FIG. 11 electrosurgical device 400 includes a vacuum tube 403 disposed above an electrode 405. The electrode 405 is supported by an electrode holder 410. The body 415 of the device 400 has buttons 430 and 435 disposed thereon for the cut and coagulate functions. The vacuum tube 403 slides in and out of the body 415 and can be locked into position by a sliding lock 425. In FIG. 12 electrosurgical device 500 includes a vacuum tube 503 disposed above an electrode 505. The electrode 505 is supported by an electrode holder 510. The body 515 of the device 500 has buttons 530 and 535 disposed thereon for the cut and coagulate functions. The vacuum tube 503 slides in and out of the body 515 and can be locked into position by a folding lock 525. In FIG. 13 electrosurgical device 600 includes a vacuum tube 603 disposed above an electrode 605. The electrode 605 is supported by an electrode holder 610. The body 615 of the device 600 has buttons 630 and 635 disposed thereon for the cut and coagulate functions. The vacuum tube 603 slides in and out of the body 615 and can be locked into position by a folding lock 625. In FIG. 14 electrosurgical device 700 includes a vacuum tube 703 disposed above an electrode 705. The electrode 705 is supported by an electrode holder 710. The body 715 of the device 700 has buttons 730 and 735 disposed thereon for the cut and coagulate functions. The vacuum tube 703 slides in and out of the body 615 and can be locked into position by a twisting lock 725. The body 715 has a grip 720 disposed thereon. In FIG. 15 electrosurgical device 800 includes a vacuum tube 803 disposed above an electrode 805. The body 815 of the device 800 has a rocker switch 818 disposed thereon for the cut and coagulate functions. The vacuum tube 803 slides in and out of the body 815 and can be locked into position.

The embodiments disclosed resulted in a number of unexpected results. By arranging the vacuum tubes above the electrode instead of below the electrode a greater portion of the smoke plume was able to be captured. Additionally, by no longer having the vacuum tube on the bottom of the electrosurgical device, the chances of injuring the patient from trauma cause by accidentally bringing the vacuum inlet nozzle onto the patient's exposed surgical site is reduced.

The user's view of the surgical site was surprisingly greatly improved by using a clear vacuum tube. Since light can easily pass through the vacuum tube, reduced amount of shadows are cast on the surgical site. Additionally, since the vacuum tube level of extension can be telescopically adjusted, an optical configuration is obtained for user's of different heights or styles of holding the electrosurgical device. Further, since not all electrodes are the same length, the vacuum tube extension can be adjusted to match the particular electrode used. The upward angled configuration of the vacuum inlet is also particularly advantageous in that it allows the suction source to get as close to the smoke generation region as possible without obstructing the user's view.

By designing the electrosurgical device such that an insulated portion of the electrode is available to be grabbed when the electrode is fully inserted, the insertion and removal of electrodes is made easier and safer. The user is less likely to get accidentally burned when changing the electrode since he/she can grid the electrode on an electrically insulated portion. Further, the use of friction ridges on the insulated portion of the electrode and the elongated body sides, the chance that the device slips in the user's hands is reduced. This is particularly important since the surgical process is likely to cause blood and other slippery body fluids to end up on the device.

The disclosed embodiments also increase surgical efficiency through the illumination offered by an attached light, the reduction of rotational strain by the external vacuum tube swivel and electrical line positioning within the swivel, and the button for controlling the vacuum source. Additionally, the RF sensor within the electrosurgical device allows the vacuum source to be automatically controlled by a circuit which is electrically isolated from the electrosurgical power supply.

Having fully disclosed the preferred form of the electrosurgical device and several variations thereof, persons skilled in the art will readily appreciate that various additional changes may be made without departing from the scope of the invention as set forth in the following claims.

The invention claimed is:

1. An electrosurgical device comprising:
an electrode;
an elongated hollow body having an internal cavity, a front end, a rear end, an external surface, and an electrical conductor arranged within said body, said hollow body configured to receive a portion of said electrode at said front end of said body such that an electrical contact is made between said electrode and said electrical conductor;
said body configured and arranged such that an insulated portion of said electrode is not surrounded by said hollow body;
a first button arranged on said external surface of said body for controlling a current flow through said electrical conductor at a first level;
a vacuum tube slidably engaged by said body and having an inlet generally facing said front end of said body, said vacuum tube arranged adjacent to said electrode, said vacuum tube having a shroud disposed at a distal end of said vacuum tube, said shroud operable to slidably move between an extended position and a retracted position along a surface of said vacuum tube such that said shroud circumscribes said electrode and covers said electrode in said extended position and exposes said electrode in the retracted position; and
a vacuum outlet port arranged near said rear end; and
wherein said outlet port, internal cavity, and vacuum inlet are in fluid communication with each other.

2. The electrosurgical device as set forth in claim 1, wherein said body is ergonometrically shaped to be received by a user's hand.

3. The electrosurgical device as set forth in claim 1, wherein said body is generally pencil shaped and includes friction texture on said surface.

4. The electrosurgical device as set forth in claim 1, wherein said electrode is one of a monopolar, bipolar, or sesquipolar electrode.

5. The electrosurgical device as set forth in claim 1, and further comprising a second button for controlling a current flow at a second level through said electrode.

6. The electrosurgical device as set forth in claim 5, and further comprising a third button to control a vacuum source.

7. The electrosurgical device as set forth in claim 1, and further comprising a swivel joint between said body and said outlet port.

8. The electrosurgical device as set forth in claim 7, and further comprising an electrical line passing through said swivel joint.

9. The electrosurgical device as set forth in claim 1, and further comprising a filter arranged within said internal cavity.

10. The electrosurgical device as set forth in claim 9, wherein said filter comprises an RFID tag containing filter information.

11. The electrosurgical device as set forth in claim 1, wherein said vacuum inlet comprises a circular cross section.

12. The electrosurgical device as set forth in claim 1, wherein said vacuum tube inlet has a shape that has a larger cross section than the cross section of the rest of the vacuum tube.

13. The electrosurgical device as set forth in claim 1, wherein said body comprises a first rigid material and a second material, said second material arranged on a portion of an external surface of said body.

14. The electrosurgical device as set forth in claim 13, wherein said second material is a material softer than said first material.

15. The electrosurgical device as set forth in claim 13, wherein said second material is a material with a higher surface friction coefficient than said first material.

16. An electrosurgical device comprising:
an electrode;
an elongated hollow body having an internal cavity, a front end, a rear end, an external surface, and a retractable electrode mount slidably arranged within said body, said electrode mount configured and arranged to receive said electrode;
a first button for controlling a current flow at a first level to said electrode and arranged on said external surface;
a vacuum tube slidably engaged by said body and having an inlet generally facing said front end, said vacuum tube surrounding said electrode mount, said vacuum tube having a shroud disposed at a distal end of said vacuum tube, said shroud operable to slidably move between an extended position toward said front end and a retracted position toward said rear end along a surface of said vacuum tube such that said shroud circumscribes said electrode and covers said electrode in said extended position and exposes said electrode in the retracted position;
a vacuum outlet port arranged near said rear end of said body; and
wherein said outlet port, internal cavity, and vacuum inlet are in fluid communication with each other.

17. The electrosurgical device as set forth in claim 16, wherein said hollow body is shaped to have an ergonometric shape complementary to a user's hand.

18. The electrosurgical device as set forth in claim 16, wherein said vacuum tube comprises a clear material.

19. The electrosurgical device as set forth in claim 16, wherein said retractable electrode mount is compressively engaged by said body.

20. The electrosurgical device as set forth in claim 16, wherein said electrode mount, vacuum tube, and said body are in a telescopic arrangement.

* * * * *